United States Patent
Anile

(10) Patent No.: US 9,463,306 B2
(45) Date of Patent: Oct. 11, 2016

(54) IMPLANTABLE MECHANICAL VALVE DEVICE FOR THE TREATMENT OF HYDROCEPHALUS SYNDROME

(71) Applicant: SIAD HEALTHCARE S.p.A., Assago (IT)

(72) Inventor: Carmelo Anile, Assago (IT)

(73) Assignee: SIAD HEALTHCARE S.P.A., Assago (IT)

( * ) Notice: Subject to any disclaimer, the term of this patent is extended or adjusted under 35 U.S.C. 154(b) by 95 days.

(21) Appl. No.: 14/487,146

(22) Filed: Sep. 16, 2014

(65) Prior Publication Data
US 2015/0088049 A1 Mar. 26, 2015

(30) Foreign Application Priority Data
Sep. 23, 2013 (IT) .................................. MI13A1558

(51) Int. Cl.
*A61M 5/00* (2006.01)
*A61M 27/00* (2006.01)

(52) U.S. Cl.
CPC ...... *A61M 27/006* (2013.01); *A61M 2027/004* (2013.01)

(58) Field of Classification Search
CPC ........... A61M 27/006; A61M 27/002; A61M 51/4276; A61M 2202/0464; A61M 2210/0693; A61M 2205/8287; A61B 5/031
USPC .......................................................... 604/9
See application file for complete search history.

(56) References Cited

FOREIGN PATENT DOCUMENTS

| DE | 202009012986 U1 | 2/2010 |
|---|---|---|
| EP | 1491232 A2 | 12/2004 |
| EP | 1491232 A3 | 2/2006 |
| EP | 2221083 A1 | 8/2010 |
| EP | 2253352 A1 | 11/2010 |

OTHER PUBLICATIONS

Written Opinion of Counterpart Italian Application MI20131558.

*Primary Examiner* — Philip R Wiest
(74) *Attorney, Agent, or Firm* — Silvia Salvadori, P.C.; Silvia Salvadori

(57) ABSTRACT

An implantable device for the treatment of hydrocephalus syndrome, characterized by a mechanical passive valve device designed to move the cerebrospinal fluid in the cranial site of the patient, comprising a cylindrical body, a piston, and a special spring exhibiting a non-linear characteristic and suitable for applying a force on the piston such that, when the pressure of the cerebrospinal fluid acting on the two opposite faces of the piston exceeds a certain value, a rapid displacement of the piston in the cylindrical body takes place due to the non-linear characteristic of the spring, with consequent aspiration, by the same piston, of a greater quantity of cerebrospinal fluid contained in the ventricle and, when the pressure of the cerebrospinal fluid falls below a certain value, the piston reacts and moves rapidly in a direction opposite to the first, so as to feed into the ventricle the cerebrospinal liquid previously aspirated.

8 Claims, 8 Drawing Sheets

IMPLANTABLE MECHANICAL VALVE DEVICE FOR THE TREATMENT OF HYDROCEPHALUS SYNDROME

This application is U.S. Non-Provisional application which claims priority to and the benefit of Italian Application No. MI2013A001558 filed on 23 Sep. 2013, the content of which is incorporated herein by reference in its entirety.

FIELD OF THE INVENTION

The present invention relates in general to the treatment of hydrocephalus syndrome or hydrocephalus, and more particularly its object is a mechanical device implantable in a patient in order to implement this treatment.

BACKGROUND OF THE INVENTION AND PRIOR ART

The hydrocephalus syndrome still today represents a complex and difficult challenge both as regards understanding the pathogenetic mechanisms which are at the origin thereof and as regards the identification and the implementation of the best methods of possible treatment.

Numerous pathogenetic hypotheses of hydrocephalus have been put forward over recent decades.

For completeness of information, the hypotheses that have gained and currently gain the greatest consensus will be described in brief here below.

Hypothesis of the "Circulation" of the Cerebrospinal Fluid

The first hypothesis which is also that currently most followed and accepted, is based on the assumption of a "circulation" of the cerebrospinal liquid or liquor starting from the choroid plexuses of the cerebral ventricles and with final target at the Pacchionian granulations of the cerebral convexity.

According to this hypothesis one obstacle to this "circulation" placed at any level and with any means, caused for example by acqueductal stenosis, a tumour of the posterior cranial fossa, a reduction in absorption as a result of haemorrhages or infections in the subarachnoid spaces, is at the origin both of so-called "obstructive" or "non-communicating" hydrocephalus and of the "non-obstructive" or "communicating" type.

Leaving aside, as well as considerations of a theoretical nature, a numerous series of indirect and experimental data contrary to the pathogenetic hypothesis of an obstacle to the flow of liquor, that which brought down this hypothesis definitively was the "direct" evidence, in the animal and human model, of the lack of a "circulation" of the cephalorachidian liquid, at least in the form wherein it should be in action for a mechanism of "obstacle" to this circulation to be able to produce a significant ventricular dilation.

In other words it has been extensively demonstrated, on the one hand, that a "diffusion" exists and not a displacement of volume (i.e. a "circulation") of the liquor inside the intracranial system, in such a way that the same sites of production of the liquor are also assigned its absorption and, on the other hand, the movement of the liquor inside and outside the ventricular cavities is made up of a periodical oscillation synchronous with the heartbeat, but "without" a real "clear flow" in one direction or in the other.

This conclusion is reached also by extensive medical literature on the subject, supported by experimental data, bearing in mind that the fundamental variable to be considered, in the analysis of these data, is always the "rate" of the flow, i.e. the so-called "signal void".

In fact the item of data obtained with experimental measurement has to be appropriately corrected so as to take account of the variation in calibre of the structure (usually the aqueduct of Sylvius) in which the measurement is taken, which, as is known, periodically thins in systole, thus causing an increase in the speed (but not of the flow) and widens in diastole, thus causing an opposite effect such as to compensate exactly the previous one, thus reconfirming the lack of a "clear flow" and, therefore, of a real "circulation" of cerebrospinal fluid (CSF).

Hypothesis of "Ventricular Pulsatility"

The second hypothesis is based on the observation that a condition of hydrocephalus, both clinical and experimental, is very often associated with an increase in the so-called "CSF pulsatile pressure", i.e. in the difference between the maximum value and the minimum value of the intracranial pressure during every cardiac cycle.

Going into depth as regards this second hypothesis, on the basis of a model of intracranial system with rigidly constant volume, a different explanation can be put forward for the onset of the hydrocephalus syndrome, for which the development of the hydrocephalus, of whatever type it is, irrespective of its aetiology, is produced by the association between the "intraventricular pulsatility of the choroid plexuses" and an "asymmetric response" of the brain parenchyma.

In particular this second hypothesis take account of a behavioural feature well known in literature as regards "visco-elastic" substances, to which the brain parenchyma has always been compared on the anatomic-structural level.

This means that the brain, with respect to the actual pulsating force acting thereon, is more easily "compressible" (in systole) than it is "distensible" (in diastole) at the end of the phase of compression.

The continuing alternation between systole (compression) and diastole (distension) causes a progressive reduction in the volume of the brain, and therefore an increase in the ventricular volume, up to a new point of equilibrium between the forces acting in the two directions which will determine the current dimensions of the cerebral ventricles, from normal or relatively normal volumes up to the extreme degrees of the hydrocephalus syndrome.

From what has been disclosed it is clear how the systems of treatment of hydrocephalus currently in use and based, fundamentally, on the use of so-called "CSF shunts", i.e. on the displacement of part of the CSF volume from the intracranial system towards other cavities of the body, cannot correspond, except partially, indirectly and inaccurately, to the solution of the pathogenetic alteration, as hypothesised here.

This incongruity clearly explains, moreover, the limitations still present in the traditional treatment of hydrocephalus syndrome.

A radical solution to the problem appears possible only by acting on one of the two factors, or both, which were illustrated previously, i.e. the "intraventricular pulsatility" and the "asymmetric response" of the brain parenchyma.

Reference to Previous Patent Applications Designating the Same Inventor

In the same field of the present invention, i.e. of the treatment of hydrocephalus syndrome and the devices which can be used in this treatment, mention is made of the following two previous patent applications, both designating the same inventor as the current patent application:

No. RM2006A00592, filed on 2 Nov. 2006 and granted with No. 0001372554, entitled "IMPLANTABLE DEVICE FOR THE TREATMENT OF HYDROCEPHALUS SYNDROME" and No. MI2012A000097 of 27 Jan. 2012, entitled "IMPROVED IMPLANTABLE DEVICE FOR THE TREATMENT OF HYDROCEPHALUS SYNDROME AND CORRESPONDING METHOD".

These two previous patent applications, basing on the context previously set out and on the various hypotheses, in particular the second, "which were formulated to justify the treatment adopted for hydrocephalus syndrome, propose a rotary volumetric micro pump which, appropriately actuated, removes liquor from the cranial site and moves it into an accumulator, when it is necessary to reduce the actual value of the intracranial pressure or ICP, and reintroduces it into the cranial site when it is instead necessary to increase the instantaneous value thereof.

The systems described in these previous patent applications refer to and comprise, as an essential part, electric devices with electronic components.

The present patent application is instead aimed at a system or device suitable for obtaining the same benefit of treatment of hydrocephalus by means of the use of exclusively mechanical devices, therefore without the use of electric or electronic parts.

OBJECTS AND SUMMARY OF THE INVENTION

Therefore the present invention sets primarily the aim of bringing significant and tangible improvements in the treatment of hydrocephalus syndrome and, in particular, in this intent, to provide a device, implantable in a patient as part of this treatment, which, using a device of exclusively mechanical type, allows the intraventricular pulsation to be attenuated significantly.

These objects can be considered fully achieved by the device implantable in a patient for the treatment of hydrocephalus syndrome, having the features defined by the independent claim 1.

Particular embodiments of the present invention are defined by the dependent claims.

Advantages of the Invention

Specifically the object of the present invention is an implantable device for the treatment of hydrocephalus syndrome which is aimed at modifying the pulsation, reducing the amplitude thereof, of the intracranial pressure generated in the cranial bones by the cardiac pulsation.

In order to achieve this object the device of the invention is based on purely mechanical features.

Moreover the device is presented as suitable for damping the liquor pulsations as a function of the real needs required by the hydrocephalus syndrome in every particular moment of daily living.

Therefore the device that forms the object of the present invention offers important advantages and improvements with respect to the implantable devices described in the previous patent applications, cited previously, and in particular obtains the same results without however being affected by the same disadvantages, being in particular constituted by purely mechanical elements which do not require electrical power supply and electronic components.

BRIEF DESCRIPTION OF THE DRAWINGS

These and other objects, features, modes of use and advantages of the present invention will be made clear and evident by the following description of one of its preferred embodiments, given by way of a non-limiting example, with reference to the accompanying drawings, in which:

FIGS. 3A-3K are working diagrams and schemes concerning the general features and some possible embodiments of the special spring of FIG. 2, with non-linear elastic characteristic, an essential part of the device of the invention;

Figure 1:
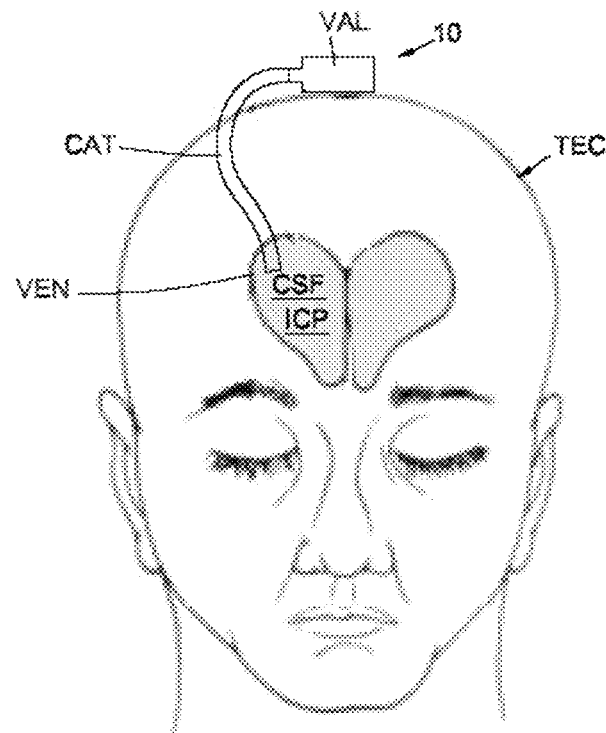
FIG. 1 is a schematic view of a patient in which a mechanical device, in accordance with the present invention, has been implanted for the treatment of the hydrocephalus syndrome.

DESCRIPTION OF SOME PREFERRED EMBODIMENTS OF THE MECHANICAL IMPLANTABLE DEVICE OF THE INVENTION FOR THE TREATMENT OF HYDROCEPHALUS SYNDROME

Referring to the drawings, a device, according to the present invention, for the treatment of hydrocephalus syndrome, is denoted overall by 10.

The device 10 of the invention, for the treatment of hydrocephalus syndrome, has completely mechanical features and, as shown in FIG. 1, is suitable for being implanted surgically in the cranial site TEC of a patient, affected by hydrocephalus.

In particular, as can be seen again from FIG. 1, the device 10, once implanted by the surgeon in the cranial site TEC, is provided for communicating on one side, via a catheter CAT, with the interior of a cerebral ventricle VEN of the patient, affected by hydrocephalus, so as to receive the cerebrospinal fluid CSF or liquor, in the same ventricle VEN, and the respective intracranial pressure ICP.

For the sake of clarity, before describing some possible embodiments of the device 10, a description will be given of the principle, the technical concepts, the parts and the essential features which are at the basis thereof and of its functioning.

General Principle of Functioning and Essential Features of the Mechanical Implantable Device of the Invention.

Figure 2:
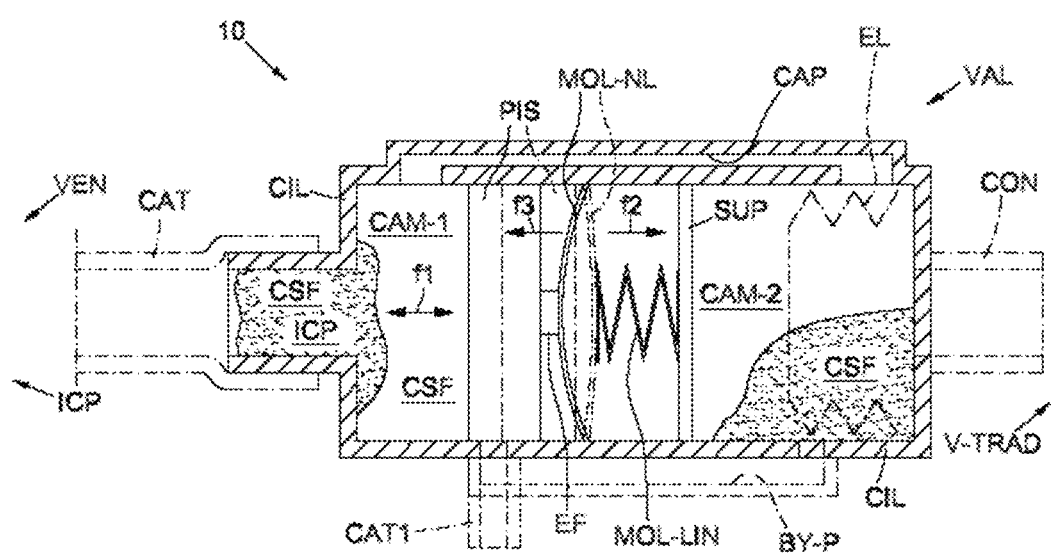
FIG. 2 is a general diagram which shows the essential elements of a mechanical valve assembly or device including a special spring, exhibiting a non-linear elastic characteristic, which constitutes the fundamental part of the implantable device of the present invention for the treatment of the hydrocephalus syndrome.

As shown in the general scheme of FIG. 2, the device 10 of the invention is essentially constituted by a passive mechanical valve, denoted overall by VAL, comprising:
- an external cylinder or cylindrical body CIL, hollow, also simply referred to as cylinder;
- a piston PIS housed and suitable for sliding in the two directions in the cylinder or body CIL, as indicated by a double arrow f1, so as to divide the space of the internal cavity of the cylinder CIL into two separate chambers, frontal and rear, denoted respectively by CAM-1 and CAM-2; and
- a non-linear spring, denoted by MOL-NL, also housed inside the cylindrical body CIL and exhibiting a special non-linear characteristic, described here below in detail, wherein this non-linear spring MOL-NL is associated with and suitable for co-operating with the piston PIS to control it and hold it in position in the cylinder CIL.

The piston PIS can also be made in the form of a membrane, deformable, also suitable for dividing into separate chambers CAM-1 and CAM-2 the space of the internal cavity of the cylinder CIL and to perform the same function of the sliding piston PIS, so that it is specified that here below in the description the term "piston" has to be interpreted as equivalent also of the term "membrane".

The cylinder or cylindrical body CIL communicates on the one side, in particular that of the respective frontal chamber CAM-1 wherein its internal cavity is divided by the sliding piston PIS, with the ventricle VEN by means of a catheter CAT.

Therefore, by means of the catheter CAT, the valve VAL is suitable for receiving the cerebrospinal fluid CSF, contained in the ventricle VEN, and the piston PIS is suitable for being subject to the intracranial pressure ICP present in the same ventricle VEN.

The zone of this frontal chamber CAM-1 of the valve VAL and of the cylinder CIL, in communication with the ventricle VEN, can have various configurations as a function of the specific embodiment of the device 10, as described here below, and in particular can be in communication, as well as with the ventricle VEN by means of the catheter CAT, also with a further drainage catheter CAT1, represented by a dashed and dotted line in FIG. 2.

The zone of the other rear chamber CAM-2 of the cylinder CIL, placed with respect to the frontal chamber CAM-1 on the opposite side of the piston PIS, can have various configurations, described in detail here below, as a function of the specific embodiment of the device 10.

In particular the rear chamber CAM-2 can be closed, as shown by an unbroken line in FIG. 2, and in this case house a yielding element EL, schematised with a dashed and dotted line in the same FIG. 2.

Or the rear chamber CAM-2 can be in communication, by means of a duct CON represented by a dashed and dotted line, with a traditional shunt valve V-TRAD, not shown but only indicated by an arrow in FIG. 2, of the "differential" or threshold type, aimed at maintaining the chamber CAM-2 at a constant average pressure and having the same functions as shunt valves currently used in the treatment of hydrocephalus.

A capillary tube CAP is always provided, in all the embodiments of the device 10, for enabling communication between the two chambers CAM-1 and CAM-2 and thereby allowing the cerebrospinal fluid CSF to flow between them.

Moreover a bypass tube, denoted by BY-P and represented with a dashed and dotted line in FIG. 2, can be further provided for placing in communication the two frontal and rear chambers CAM-1 and CAM-2.

Again, a further recovery spring, denoted by MOL-LIN, exhibiting a usual linear elastic characteristic, can be associated and co-operate, during functioning of the valve VAL, with the spring MOL-NL exhibiting the non-linear characteristic.

Therefore, on the basis of the configuration of the device 10 previously described and shown in FIG. 1, the opposite faces of the piston PIS, or of the membrane MEM, are subjected to a different pressure between that, present in the chamber CAM-1, in turn directly dependent on the intracranial pressure ICP acting in the ventricle VEN, and that present in the chamber CAM-2, for example determined and guaranteed by the traditional shunt valve V-TRAD.

Consequently, when the difference in pressure between the two faces of the sliding piston PIS is null, the piston PIS tends to position, at the ends of its stroke in the cylindrical body CIL, in a stable rest configuration, in which the piston PIS is held stably by the spring MOL-NL, exhibiting the special non-linear characteristic, also placed in a stable end configuration.

When instead the intracranial pressure ICP present in the ventricle VEN tends to grow, during the phase of cardiac systole, the piston PIS, being subject to a greater pressure on the side facing onto the front chamber CAM-1, reacts by moving from right to left in FIG. 2, or in the direction of the rear chamber CAM-2, deforming consequently the spring MOL-NL which in turn reacts by applying an elastic force on the piston PIS.

Therefore, in the continuation of the systolic phase, when the difference in pressure of the cerebrospinal fluid CSF which acts on the two opposite faces of the piston PIS exceeds a certain value, in turn defined during the phase of calibration and manufacture of the passive valve VAL and dependent on the specific non-linear elastic characteristic of the spring MOL-NL associated with the piston PIS, the spring MOL-NL due to the very effect of this non-linear characteristic thereof trips rapidly from one side towards the chamber CAM-2, as indicated by an arrow f2 in FIG. 2.

Consequently the piston PIS is also driven and pushed by the spring MOL-NL to move rapidly from left to right in the direction of the chamber CAM-2, in particular kept at constant pressure by the traditional shunt valve.

In this way the piston PIS moves and aspirates from the ventricle VEN a volume of cerebrospinal liquid CSF which is significantly larger than that which would have been aspirated should the spring, associated with the piston PIS, have had a normal linear characteristic and therefore the piston PIS not have had this rapid movement towards the chamber CAM-2, so that an appreciative and significant reduction is produced, during the systolic phase, in the ventricle VEN, in the intracranial pressure ICP with respect to that which would have occurred in normal conditions, i.e. in the absence of the device 10 of the invention.

Again, when the intracranial pressure ICP present in the ventricle VEN falls below a certain value, during the successive phase of cardiac diastole, both due to the same cardiac diastole and due to the aspiration of the cerebrospinal fluid CSF, the piston PIS returns rapidly into the previous rest position, at the other end of its stroke in the cylinder CIL, under the control of the spring MOL-NL which trips to the left from the position previously reached, as indicated by an arrow f3.

In this way the piston PIS infuses and feeds again into the ventricle VEN the cerebrospinal liquid previously aspirated and extracted, thus producing an increase in the intracranial pressure ICP, in the diastolic phase, in the ventricle VEN, with respect to the intracranial pressure which would have occurred in normal conditions, i.e. in the absence of the device 10 of the invention.

Consequently the overall effect produced by the device 10 is an appreciative and important reduction in the intracranial pressure ICP during the systolic phase and an increase during the diastolic one, i.e. a reduction in the intraventricular pulsatility, i.e. of the change of the intracranial pressure ICP in the ventricle VEN, with respect to the normal conditions in the absence of the device 10, maintaining substantially unchanged the average value of the intracranial pressure ICP.

From what has been set out above it clearly emerges that the element and the fundamental part of this passive valve VAL, which constitutes the device 10 of the invention, is the return spring MOL-NL with non-linear characteristic.

Therefore, for a complete description of the invention, a detailed description will be given of the parameters and the magnitudes which define this spring MOL-NL and its special non-linear characteristic.

Figure 3A:
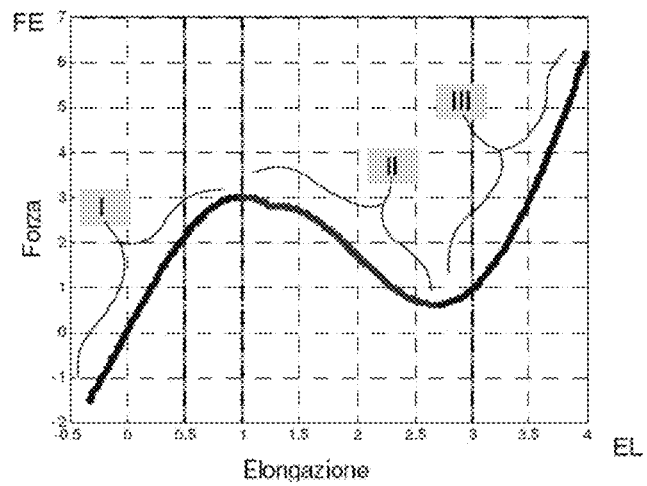
Figure 3B:
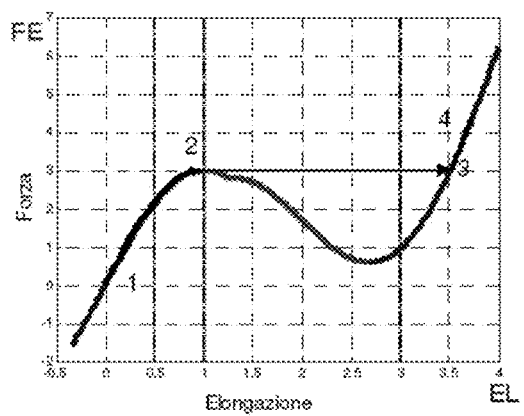
Figure 3C:
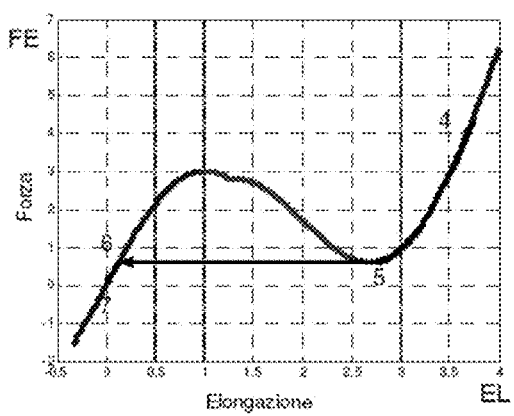

General Description of the Non-Linear Bistable Spring which Characterises the Device of the Invention The non-linear spring MOL-NL, an essential part of the implantable device 10 of the invention for the treatment of hydrocephalus syndrome and of the respective mechanical valve VAL, has a force/elongation characteristic having a trend qualitatively similar to that shown in the diagrams of FIGS. 3A, 3B and 3C of the drawings.

In particular in these diagrams as the abscissa the elongation is plotted, denoted by EL, of the non-linear spring MOL-NL starting from the respective position of rest defined by a null abscissa, i.e. EL=0, while plotted as the ordinate is the corresponding elastic force FE with which the spring MOL-NL reacts during its elongation, i.e. the force which has to be exerted on one side of the same spring MOL-NL in order to deform it and therefore cause its elongation.

This elongation EL and this elastic force FE in turn correspond, the non-linear spring MOL-NL being coupled on one side with the sliding piston PIS, respectively to the displacement of the piston PIS from its rest position, and to the net force acting on the piston PIS, in turn deriving from and defined by the difference in pressure acting on the two opposite faces of the same piston PIS.

Therefore a positive elongation of the spring MOL-NL, starting from the position of abscissa=0, occurs when the pressure, internal, which acts on the face of the piston PIS facing onto the frontal chamber CAM-1 and corresponds to the intracranial pressure ICP in the ventricle VEN, is greater than the pressure, external, which acts on the opposite face of the piston PIS and is for example controlled by the shunt valve of traditional type V-TRAD.

In the non-linear characteristic of the spring MOL-NL, as shown in FIG. 3A, it is possible to distinguish various zones, and in particular a first zone I, with positive gradient, starting from the position of rest of abscissa El=0, in which an increase in elongation EL of the spring MOL-NL corresponds to an increase in the force FE applied thereon. A successive second intermediate region II, with negative gradient, in which instead an increase in elongation EL of the spring MOL-NL corresponds to a decrease in the force applied FE. Finally a successive third zone III, again with positive gradient.

The intermediate region II of this non-linear characteristic of the spring MOL-NL is therefore a region in which the respective points are associated with a condition of instable equilibrium, of the same spring MOL-NL.

On the whole this non-linear and instable characteristic of the spring MOL-NL produces a series of effects, as described here below, on the motion of the piston PIS, with which the spring MOL-NL is associated and co-operates.

As can be seen from the diagram of FIG. 3B, during the cardiac systole phase, the non-linear spring MOL-NL co-operates with the piston PIS, to control its position, traversing the respective characteristic in the following sequence of points 1-2-3-4.

Therefore in the section 1-2 the elongation of the spring MOL-NL increases gradually as the force applied thereon by the piston PIS increases.

Then, when the force F exceeds a certain value, corresponding to point 2, a rapid transition occurs between points 2 and 3, with a consequent rapid displacement of the piston PIS towards the region with lower pressure, i.e. towards the chamber CAM-2.

This rapid displacement of the piston PIS also causes a corresponding and equally rapid aspiration of the cerebrospinal fluid CSF from the ventricle VEN, with a consequent decrease in the instantaneous intracranial pressure ICP.

The section between points 3 and 4 is traversed by the spring MOL-NL and by the piston PIS only if the intracranial pressure ICP is not reduced adequately, so that, in the normal functioning of the valve VAL with an adequate reduction in the intracranial pressure ICP, this section 3-4 is not usually traversed and the elongation of the spring MOL-NL, i.e. the stroke of the piston PIS, ends approximately at point 3 of FIG. 3B.

When instead, during the phase of cardiac diastole, the intracranial pressure ICP is reduced in the ventricle VEN both due to the actual diastolic phase and due to the action of the valve VAL, the spring MOL-NL traverses the respective non-linear characteristic, to control the position of the piston PIS, according to the points 4-5-6-7, as shown in FIG. 3C, i.e. in reverse direction with respect to FIG. 3B, corresponding to the systolic phase.

Therefore in the section between 4 and 5 the reduction in the intracranial pressure ICP causes a gradual displacement of the piston PIS in the direction towards the chamber CAM-1 of the valve VAL.

Then, when the intracranial pressure ICP drops below a certain value corresponding to point 5, the spring trips rapidly towards the null elongation position, i.e. EL=0.

Consequently the piston PIS also has a rapid displacement towards its rest position, so as to end a rapid infusion and feeding of cerebrospinal fluid CSF into the ventricle VEN and therefore also an increase in the instantaneous intracranial pressure ICP.

It is pointed out that, in the functioning of the device of the invention 10, the non-linear characteristic of the spring MOL-NL is traversed according to the methods first illustrated with reference to FIGS. 3B and 3C, supposing that the device of the invention 10 operates in nominal conditions of substantial equilibrium and that the pressure acting on the piston PIS does not depend on and is not significantly influenced by the dynamic stresses exerted by the displacement of the mass of the same piston PIS.

Figure 3D:
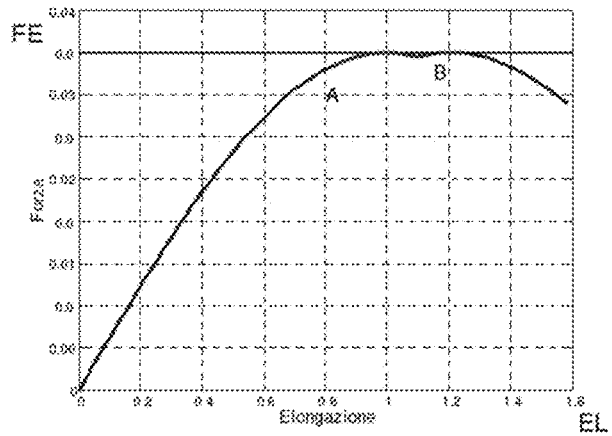

Effectively, taking account of the dynamic interaction between the displacement of the piston PIS and the intracranial pressure ICP, it can be imagined that in real conditions the force/elongation characteristic of the non-linear spring MOL-NL assumes a trend similar to that shown in FIG. 3D and that therefore the spring MOL-NL in the zone of instability traverses the section A-B of this characteristic.

As can be seen, in this section A-B of the non-linear characteristic of the spring MOL-NL small variations in the pressure acting on the piston PIS correspond and give rise to major displacements of the same piston PIS, i.e. to a considerable elongation EL of the non-linear spring MOL-NL so as to produce important effects on the intracranial pressure ICP.

Embodiments of the Spring with Non-Linear Elastic Characteristic

Within the sphere of the present invention, various solutions are possible and can be foreseen for manufacturing an implantable valve device 10, such as that described previously in its basic essential concepts, and in particular in order to manufacture a bistable spring MOL-NL, or in general a spring system, exhibiting a non-linear elastic characteristic with a negative or null gradient section, which definitely constitutes the most important part of this valve device 10.

Figure 3E:
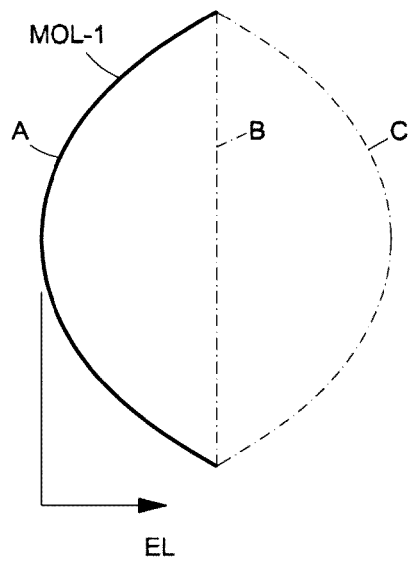
Figure 3E:
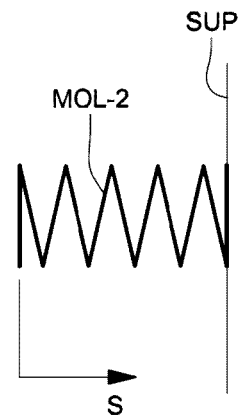

A first possible solution for making such a non-linear elastic system foresees the use of two springs, in combination, denoted respectively by MOL-1 and MOL-2 and shown in section respectively in the left zone and in the right zone of FIG. 3E.

In particular the first spring MOL-1 is constituted by an elastic spherical cap, shown in section in FIG. 3E with a smaller radius of curvature than normal to highlight the functioning thereof, which has two end configurations or points, denoted by A and C, in which the spring MOL-1 is in stable equilibrium, and an intermediate configuration B, in which the spring MOL-1 is in instable equilibrium and which the same spring MOL-1 assumes when it is moved from configuration A to the C one and vice versa.

Therefore the spring MOL-1 has a bistable functioning and one of its minor displacements or disturbances, when it is in the intermediate instable configuration B, causes an immediate displacement of the same spring MOL-1 towards the stable end configuration A or C.

Figure 3F:
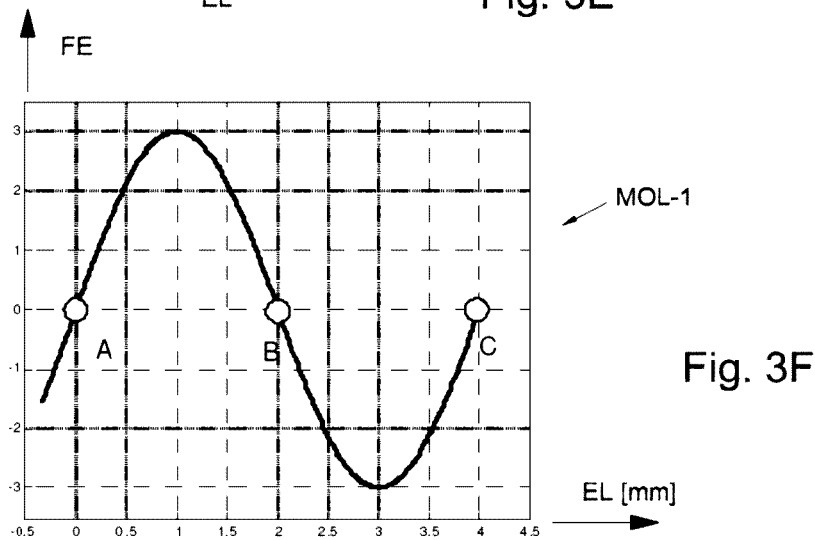

More particularly the diagram of FIG. 3F shows the non-linear force F/elongation E characteristic which characterises this spring MOL-1 and its bistable functioning when it moves and displaces, i.e. it has an elongation E starting from the starting configuration A, between the two stable end configurations A and C passing through the instable intermediate configuration B.

Figure 3G:
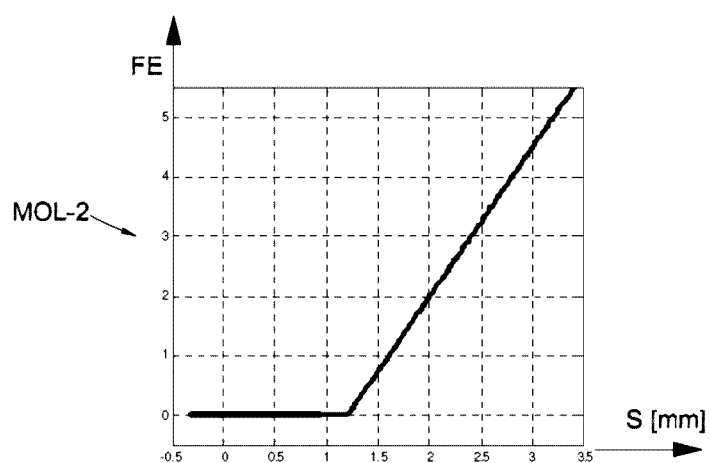

The second spring MOL-2 on the right in FIG. 3E is instead a compression spring which has a usual linear characteristic, as shown in the diagram of FIG. 3G, i.e. it is a spring which, if compressed at one end, reacts with an elastic force F which grows linearly with the displacement S starting from an initial configuration, not compressed and undeformed, of the spring MOL-2.

Figure 3H:
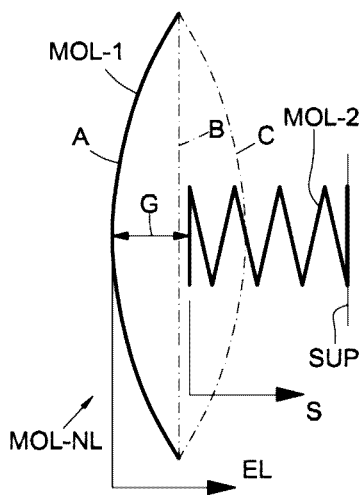

These two springs MOL-1 and MOL-2 are combined and coupled one with the other, providing a certain play G between the stable configuration A of the non-linear spring MOL-1 and the initial undeformed configuration of the linear compression spring MOL-2, as shown in FIG. 3H.

Figure 3I:
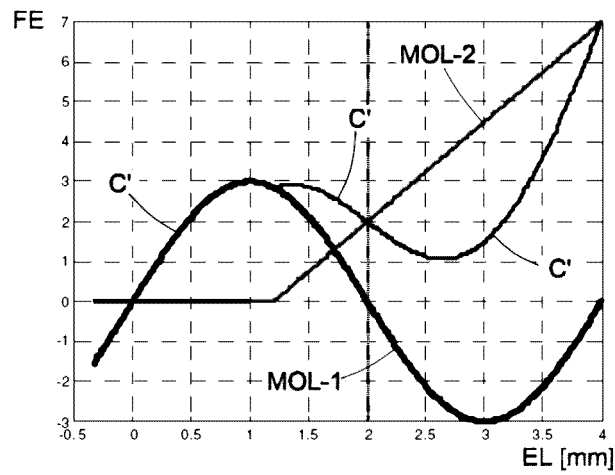

Therefore, by combining the two characteristics of the springs MOL-1 and MOL-2, the final non-linear characteristic is obtained, denoted by C' in FIG. 3I.

As can be seen in FIG. 3I the linear characteristic of the spring MOL-2 influences and modifies a significant portion of the characteristic C', and in particular appears to have a recovery effect suitable for speeding up the return of the non-linear spring MOL-1 from the left stable configuration or position C to the left initial stable configuration A, passing through the intermediate position B.

This non-linear elastic system formed by the two springs MOL-1 and MOL-2 is associated, in the valve VAL, with the piston PIS sliding in the cylinder CIL, as shown in FIG. 2, in which the springs MOL-NL and MOL-LIN correspond respectively to the non-linear spring MOL-1 and to the linear one MOL-2.

In particular the spring MOL-NL i.e. the non-linear spring MOL-1, in the form of spherical cap, is attached centrally by means of a fastening element EF with the piston PIS and along its circular edge on the surface of the internal cavity of the cylindrical body CIL, while the spring MOL-LIN i.e. the linear compression spring MOL-2 is supported at one end by a support SUP which is also in turn attached to the surface of the internal cavity of the cylindrical body CIL.

A possible alternative solution to that, described previously, of using two springs, of which one with non-linear elastic characteristic and the second with linear elastic characteristic, provides instead for the use of a single spring or membrane shaped in such a way that the respective moment of inertia, which determines the rigidity thereof, varies appropriately with the deformation of the spring.

Figure 3K:
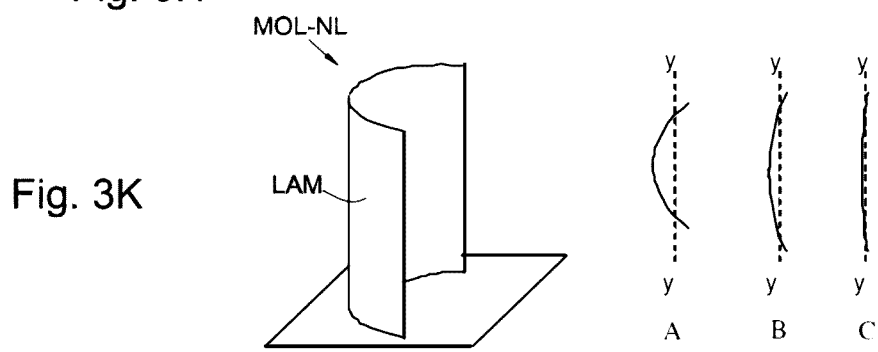

An exemplary embodiment of a single spring or membrane of this type is schematically shown in FIG. 3K and provides for the spring to be constituted by a single lamina LAM, in metallic material, shaped with cylindrical sector.

As can be seen from FIG. 3K, this metallic lamina LAM, with cylindrical sector, is such that, at the variation of its deformation or displacement starting from a stable initial configuration A, the moment of inertia of its cross section with respect to the axis Y-Y', perpendicular to this displacement, reduces progressively.

It is therefore possible to configure the metallic lamina LAM, in such a way that, when it deforms from the configuration A to the configuration C passing through the intermediate configuration B there is a non-linear variation of this moment of inertia, with respect to the axis Y-Y', and for example it varies more rapidly passing from the configuration B to the configuration C, so as to achieve the non-linear elastic characteristic of the metallic lamina LAM.

Description of Some Preferred Embodiments of the Mechanical Implantable Device of the Invention for the Treatment of Hydrocephalus Syndrome As anticipated, various embodiments are possible, described in detail here below, whereby the implantable device 10 of the invention, always connected on one side by means of a catheter CAT with the ventricle VEN in order to receive the intracranial pressure ICP present in the same ventricle VEN, can be made.

First Embodiment of the Mechanical Implantable Device of the Invention

Figure 4:
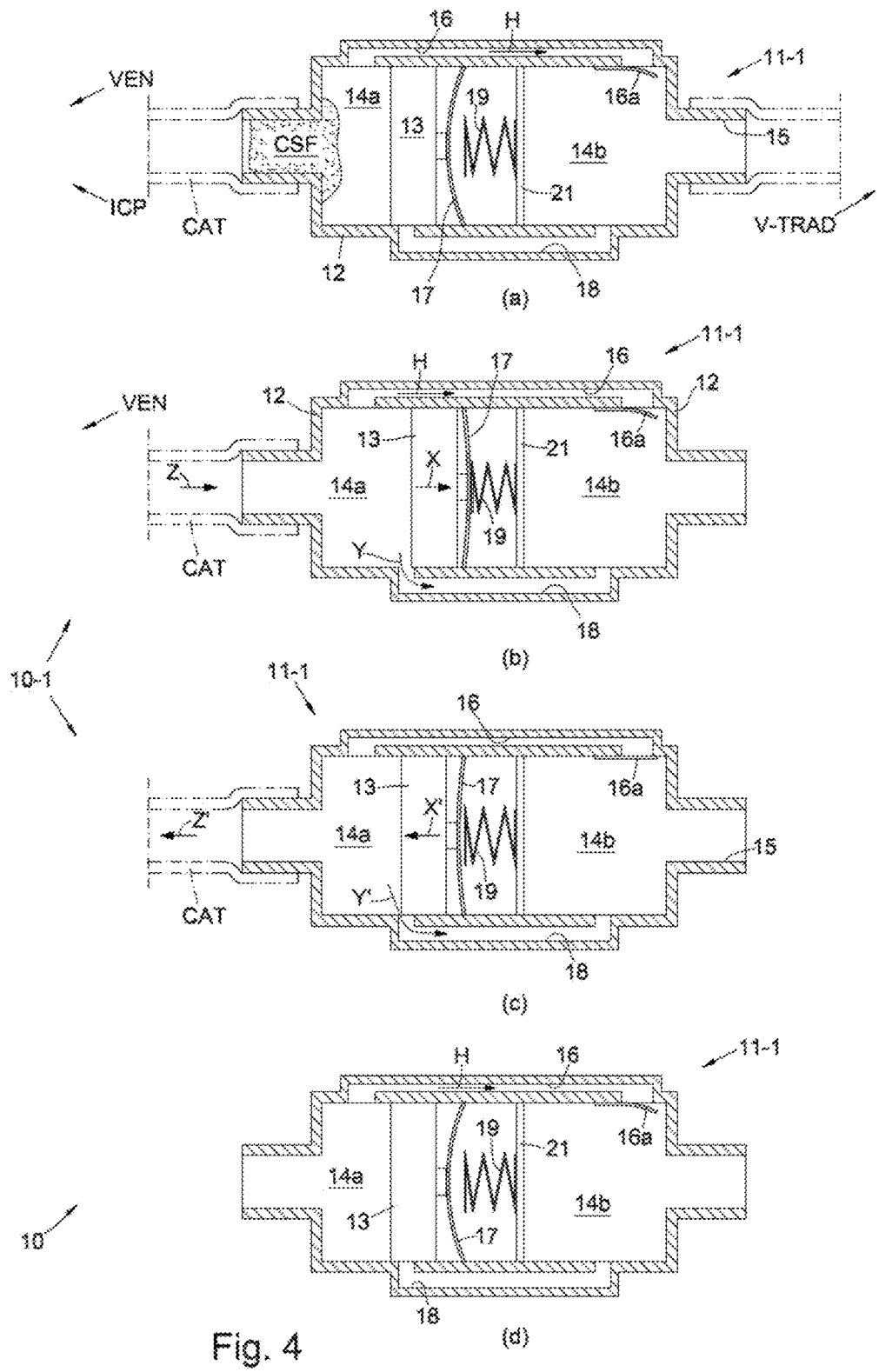
FIG. 4, divided into the sections (a)-(d), shows a first embodiment of the mechanical device of FIGS. 1 and 2, for the treatment of the hydrocephalus syndrome, in the various configurations taken on by the device during its functioning.

According to this first embodiment, denoted by 10-1 and shown in FIG. 4, the device of the invention, in addition to being connected on one side with the ventricle VEN of the cranial site by means of the catheter CAT, is connected on the opposite side by means of an opening 15 with a traditional valve V-TRAD of the "differential" or threshold type, which has the same functions as the shunt valves currently used in the treatment of hydrocephalus and whose purpose is that of providing a constant and known reference pressure.

In detail the device 10-1 comprises a valve assembly or device, denoted overall by 11-1, corresponding to the valve VAL, mechanical, of the general scheme of FIG. 2 and in turn including:

an external, hollow, cylindrical body 12, corresponding to the cylinder C of FIG. 2;

a piston 13, sliding in the cylindrical body 12 and corresponding to the piston PIS of FIG. 2, wherein this piston 13 divides the internal volume of the cylindrical body 12 into two frontal and rear chambers, 14a and 14b, in turn corresponding to the chambers CAM-1 and CAM-2 of FIG. 2 and communicating respectively with the ventricle VEN, by means of the catheter CAT, and with the traditional valve V-TRAD which ensures a constant reference pressure; and a spring 17, exhibiting a non-linear or bistable characteristic, as described previously, and corresponding to the spring MOL-NL of FIG. 2 and to the spring MOL-1 of FIGS. 3E and 3H, wherein this non-linear spring 17 is associated with the piston 13 so as to control its position and movement while it slides inside the cylindrical body 12 and therefore modify, as described previously, the form of the pulsation of the intracranial pressure ICP due to the cardiac cycle, reducing its amplitude.

A compression spring 19, housed inside the cylindrical body 12 and supported at one end by a support 21, having a linear elastic characteristic and corresponding to the spring MOL-LIN of FIG. 2 and to the spring MOL-2 of FIGS. 3E and 3H, is associated with the non-linear spring 17 so as to co-operate with the latter in order to control the position and the movement of the piston 13.

Moreover the valve device 11-1 specifically comprises, as characteristic parts which distinguish it from other embodiments:

a capillary tube 16, formed in the cylindrical body 12 and corresponding to the capillary tube CAP of FIG. 2, wherein this capillary tube 16 is suitable for placing in communication the two chambers 14a and 14b, so as to allow the flow of the cerebrospinal fluid CSF between them and therefore also the regular functioning of the traditional threshold valve V-TRAD in communication with the rear chamber 14b;

a membrane valve 16a placed in the zone of outlet of the capillary tube 16 in the chamber 14b, in which this membrane valve 16a serves to prevent the back flow of the cerebrospinal fluid CSF from right to left in FIG. 4, i.e. from the rear chamber 14b to the front one 14a, through the capillary 16; and a connection duct 18, also referred to as bypass duct, corresponding to the duct BY-P of FIG. 2, which is formed in the cylindrical body 12 so as to place in communication the frontal chamber 14a and the rear one 14b one with the other, and which serves in particular to prevent the blocking of the piston 13 in the open position, i.e. when it is moved to the right in FIG. 4, therefore in the direction of the rear chamber 14b.

During functioning the implantable device 10-1 of this first embodiment operates in the following way.

During the phase of cardiac systole the instantaneous intracranial pressure (ICP) being relatively high, the piston 13 reacts by moving from left to right, i.e. moving from the configuration shown in the section (a) of FIG. 4 to that of sect. (b) of FIG. 4, as also indicated by an arrow X.

This movement to the right of the piston 13 in turn is such as to uncover the outlet of the bypass duct in the frontal chamber 14a and then open the bypass duct 18, so as to allow the flow through it of the cerebrospinal fluid CSF from the frontal chamber 14a to the rear one 14b, as indicated by an arrow Y in FIG. 4—sect. (b).

In this way, both the rapid displacement to the right of the piston 13 induced by the non-linear characteristic of the spring 17, and the opening of the bypass duct 18, due to the displacement of the piston 13, cause the extraction and the aspiration, through the catheter CAT, of cerebrospinal fluid CSF, from the ventricle VEN of the cranial site, as indicated by an arrow Z in FIG. 4—sect. (b), with the consequent decrease in the intracranial pressure ICP in the ventricle VEN.

Therefore, during the subsequent phase of cardiac diastole, the instantaneous intracranial pressure ICP being relatively low, the piston 13 reacts by returning back, i.e. by moving from right to left as indicated by an arrow X' in FIG. 4—sect. (c), while the bypass duct 18 remains, at least partially, open.

Therefore, in this return movement of the piston 13 a partial re-infusion of the cerebrospinal fluid CSF in the ventricle VEN occurs through the catheter CAT, as indicated by an arrow Z' in FIG. 4—sect. (c), while at least one part of this cerebrospinal fluid CSF continues to be still drained to the right, i.e. from the frontal chamber 14a to the rear one 14b, through the bypass duct 18, as indicated by an arrow Y' in FIG. 4—sect. (c).

Consequently also, in the diastolic phase, due to this re-infusion of the cerebrospinal fluid CSF the intracranial pressure ICP in the ventricle VEN tends to increase.

Therefore, at the end of the diastole phase, as shown in section (d) of FIG. 4, the piston 13 returns into the initial position, closing the bypass duct 18 and completing the re-infusion of the cerebrospinal fluid CSF in the ventricle VEN, while the instantaneous intracranial pressure ICP in the ventricle VEN returns to be relatively low.

In this periodical forward and backward movement of the piston 16, caused by the difference in pressure of the cerebrospinal fluid CSF between the frontal chamber 14a and the rear one 14b and controlled by the non-linear spring 17, the membrane valve 16a associated with the capillary tube 16 opens and closes appropriately, so as to allow or otherwise the flow of the cerebrospinal fluid CSF along the capillary tube 16, as shown by arrows H in FIG. 4, and therefore also place in communication the ventricle VEN with the traditional threshold valve V-TRAD, so that it can function correctly.

Moreover, in the cyclic movement of the piston 13, the linear spring 19 co-operates with the non-linear spring 17 so as to exert on the latter an action of recovery which has the effect of making more rapid the trips of the non-linear spring 17 between the two stable end configurations, passing through the instable intermediate configuration, so as to enhance the action of aspiration and of re-infusion of the cerebrospinal fluid CSF, by the piston 13, from and into the ventricle VEN through the catheter CAT.

Therefore, as overall effect, a reduction or levelling is produced of the cyclic variation of the intracranial pressure ICP, due to the cardiac cycle, present in the ventricle VEN.

Second Embodiment of the Mechanical Implantable Device of the Invention

Figure 5:
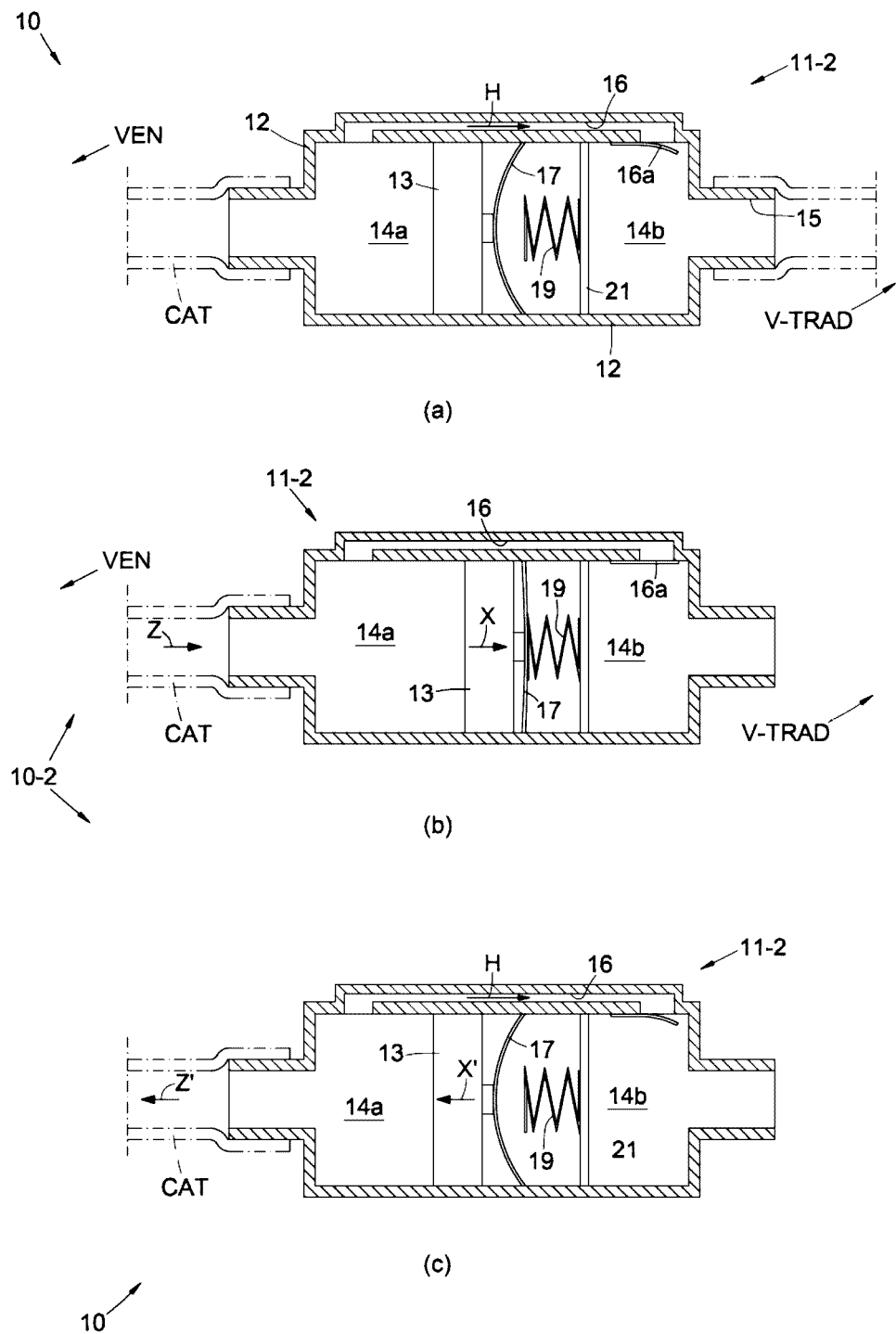
FIG. 5, divided into the sections (a)-(c), shows a second embodiment of the mechanical device of FIGS. 1 and 2, for the treatment of the hydrocephalus syndrome, in the various configurations taken on by the device during its functioning.

This second embodiment, denoted by 10-2 and shown in FIG. 5, of the implantable mechanical device of the invention is similar to the first embodiment 10-1, and differs from the latter solely by the fact that it does not provide the bypass duct or connection between the frontal chamber 14a, in turn communicating by means of the catheter CAT with the ventricle VEN of the cranial site, and the right or rear chamber 14b, in turn connected to the traditional threshold valve V-TRAD.

Therefore, in this second embodiment 10-2, the effect of levelling of the pulsation of the intracranial pressure ICP, due to the cardiac cycle, is produced and determined solely by the non-linear spring 17.

In particular FIG. 5—sect. (a) shows the valve device 11-2 of the implantable device 10-2 in an initial configuration, at the start of the cardiac phase of systole, wherein the piston 13 is placed on the right in an initial configuration.

Therefore, in the systole phase, as shown in FIG. 5—sect. (b), the instantaneous intracranial pressure ICP in the frontal chamber 14a being relatively high, the piston 13 moves to the right, compressing and deforming the non-linear spring 17.

Subsequently, again in the systole phase, when the instantaneous intracranial pressure ICP exceeds a certain value, there is, due to the non-linear characteristic of the spring 17, a rapid displacement to the right of the spring 17 and of the piston 13 connected thereto, so as to cause the aspiration of cerebrospinal fluid CSF from the ventricle VEN and consequent reduction in the instantaneous intracranial pressure ICP.

Subsequently, in the diastole phase, the intracranial pressure ICP in the frontal chamber 14a being relatively low due to the fact that this in fact is the diastole phase and due to the reduction in the intracranial pressure ICP in the preceding systole phase, the piston 13 under the control and thrust of the non-linear spring 17 returns back, moving from right to left, as shown in FIG. 5—sect. (c).

In this way the piston 13 re-infuses cerebrospinal fluid CSF in the ventricle VEN, so as to cause an increase in the instantaneous intracranial pressure ICP during the diastole phase.

Therefore, also in this second embodiment 10-2 of the implantable device 10 of the invention, the overall effect is that of reducing the intracranial pressure ICP in the systolic cardiac phase and to increase it in the diastolic phase, damping and reducing in this way the intraventricular pulsation.

In this case too the capillary 16 has the function of allowing the functioning of the traditional threshold valve V-TRAD.

Third Embodiment of the Mechanical Implantable Device of the Invention

Figure 6:
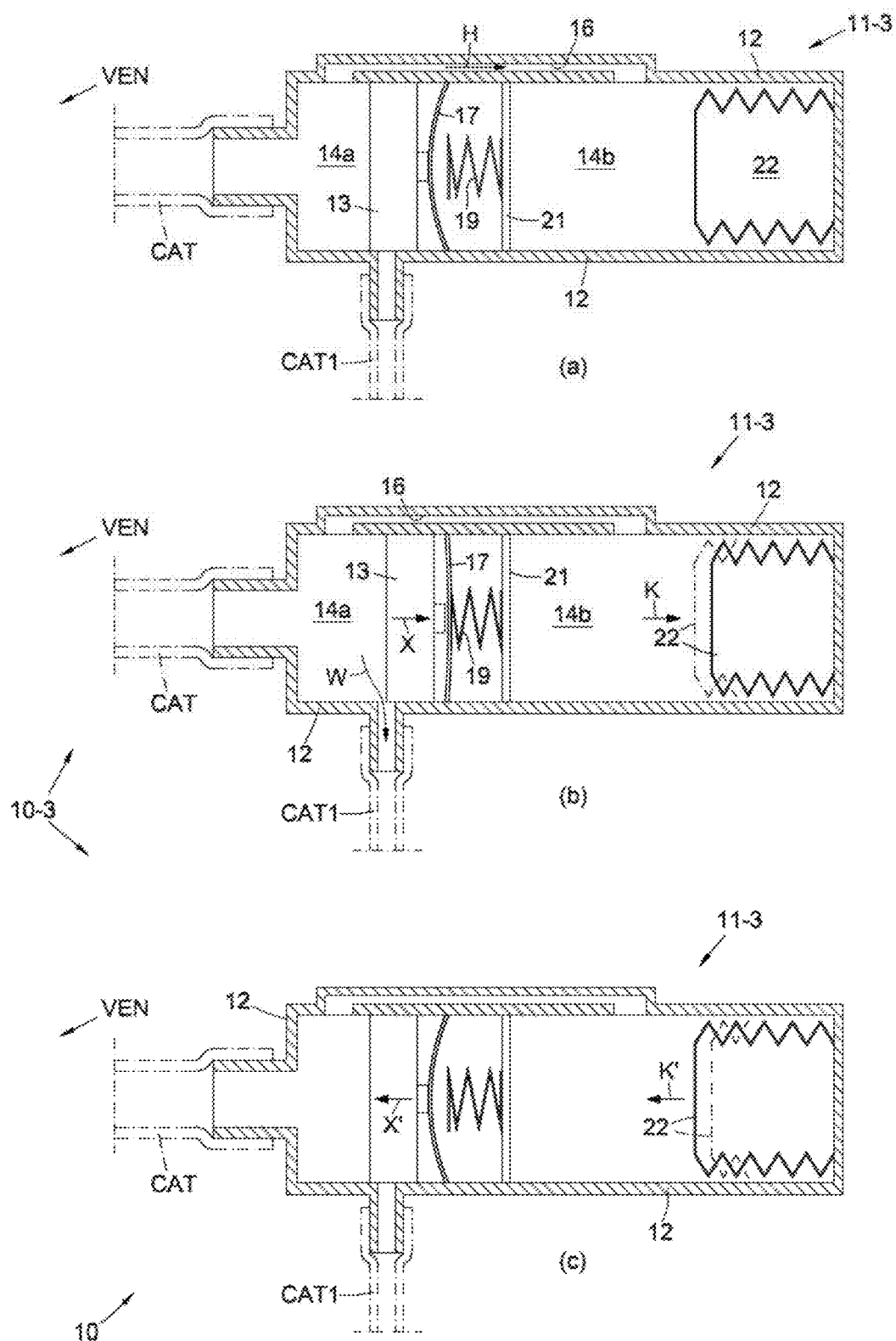
FIG. 6, divided into the sections (a)-(c), shows a third embodiment of the mechanical device of FIGS. 1 and 2, for the treatment of the hydrocephalus syndrome, in the various configurations taken on by the device during its functioning.

Referring to FIG. 6, a description will now be given of a third embodiment, denoted overall by 10-3, of the implantable device 10 of the invention, in which the parts corresponding to those of the preceding two embodiments 10-1 and 10-2 will be denoted by the same reference numerals.

In this third embodiment 10-3, similarly to the preceding two 10-1 and 10-2, the implantable device of the invention is connected on one side, in the zone of a frontal chamber 14a, with the ventricle VEN by means of a catheter CAT, and comprises a valve assembly 11-3 in turn including:

a main piston 13 sliding in a cylindrical body 12, and
a spring 17, exhibiting a non-linear characteristic associated with the sliding piston 13.

In this third embodiment 10-3, unlike the preceding two 10-1 and 10-2, the implantable device of the invention is not connected, on the side opposite that connected to the ventricle VEN, to a traditional threshold valve, but has a different configuration.

In fact the cylinder 12, wherein the piston 13 slides, forms on the side opposite to that connected to the ventricle VEN of the cranial site TEC a second chamber or rear chamber 14b, closed, which houses and contains in its interior a yielding element, denoted by 22.

In particular this yielding element 22 can be constituted by an elastic gusset, empty or filled with pressurised gas, or by a solid body of elastic material with high compressibility, such as cellular foams in rubber or synthetic materials.

Also in the valve device 11-3 of this implantable device 10-3 the two frontal and rear chambers, respectively 14a and 14b, are in reciprocal communication by means of a capillary tube 16, not associated however, unlike the preceding embodiments 10-1 and 10-2, with a membrane valve.

The piston 13 is controlled and in particular held in position of rest by a spring 17 with non-linear force-elongation characteristic similar to that described previously.

The rear chamber 14b, the gusset 22 contained in this rear chamber 14b and the capillary 16 have the function of providing a constant average pressure zone acting on a face of the sliding piston 13.

Moreover, unlike the preceding embodiments 10-1 and 10-2, the valve device 11-3 of this third embodiment 10-3 is connected in the zone of the frontal chamber 14a with a drainage catheter, denoted by CAT1 in FIG. 6, in addition to the catheter CAT which connects the same frontal chamber 14a to the ventricle VEN, in which the port of this drainage catheter CAT1 is opened or closed by the main piston 13, in its sliding in the cylindrical body 12, as shown in FIG. 6.

Before describing the effective functioning of this device 10-3 and of the respective valve assembly 11-3, in combination with the systole and diastole cardiac cycle, some preliminary considerations should be made on how the valve assembly 11-3 operates and reacts, supposing that the intracranial pressure ICP varies slowly or fast, in relation to the time constant of the same valve assembly 11-3, which in turn is determined by the hydraulic resistance of the capillary 16 and by the hydraulic capacity of the yielding element or gusset 22.

In the first case, i.e. in the hypothesis that the intracranial pressure ICP varies slowly, a flow of cerebrospinal fluid CSF is initiated through the capillary 16 which is sufficient and such as to maintain substantially equal the pressures, present in the two chambers 14a and 14b, which act on the two opposite faces of the main piston 13.

In particular, should the intracranial pressure ICP be constant, the pressure in the right frontal chamber 14a would always be identical to the intracranial one in the ventricle VEN.

Therefore, if the average intracranial pressure ICP in the ventricle VEN increases slowly, the main piston 13 remains substantially at a standstill, while the volume of the gusset or yielding element 22 reduces.

Similarly, if the average intracranial pressure ICP in the ventricle VEN decreases slowly, the main piston 13 remains still at a standstill, while the volume of the yielding element 22 increases.

If instead the average intracranial pressure ICP in the ventricle VEN varies rapidly, both while it increases and while it decreases, the effect of the capillary 16 becomes negligible, so that the piston 13 and the gusset or yielding element 22 react simultaneously, the first moving to the right or to the left, i.e. in the direction of the rear chamber 14b or of the frontal one 14a, the second deforming also to the right or to the left inside the rear chamber 14b.

Therefore the device 10-3 of this third embodiment 10-3 operates on the basis of a reference average pressure, substantially constant, which is established in the rear chamber 14b and therefore acts on the right face of the sliding piston 13, in which this reference pressure depends on the speed of variation of the intracranial pressure ICP.

Moving on to describe the effective functioning of the device 10-3, with the variation of the intracranial pressure ICP determined by the cardiac cycle, during the systole cardiac phase, due to the instantaneous intracranial pressure ICP which increases rapidly, the piston 13 moves from left to right, as indicated by an arrow X in FIG. 6—sect. (b), and simultaneously the gusset 22 deforms, shortening, also to the right, as indicated by dashed and dotted line and by an arrow K.

The displacement of the piston 13 is controlled by the non-linear spring 17, which acts as in the embodiments 10-1 and 10-2 described previously, so that this displacement to the right of the piston 13 takes place very fast, so as to cause a significant reduction in the instantaneous intracranial pressure ICP during the systole cardiac phase.

The displacement to the right of the piston 13 also causes the opening of the drainage catheter CAT1, so as to allow the drainage through it of the cerebrospinal fluid CSF, as indicated by an arrow W in FIG. 6—sect. (b).

When instead the intracranial pressure ICP decreases during the diastole cardiac phase, the piston 13 moves from right to left in order to return into the respective rest position, as indicated by an arrow X' in FIG. 6—sect. (c), while the gusset 22 too, elongating to the right, returns into the initial configuration as indicated by dashed and dotted line and by an arrow K'.

In this way the piston 13 causes the re-infusion of cerebrospinal liquid CSF in the ventricle VEN together with the closure of the drainage catheter CAT1, with the consequent increase in the instantaneous diastolic intracranial pressure ICP. Therefore, in summary, the overall effect is that of decreasing the systolic intracranial pressure ICP and making the diastolic one increase, thus damping the pulsations of the intracranial or intraventricular pressure ICP.

Fourth Embodiment of the Mechanical Implantable Device of the Invention

Figure 7:
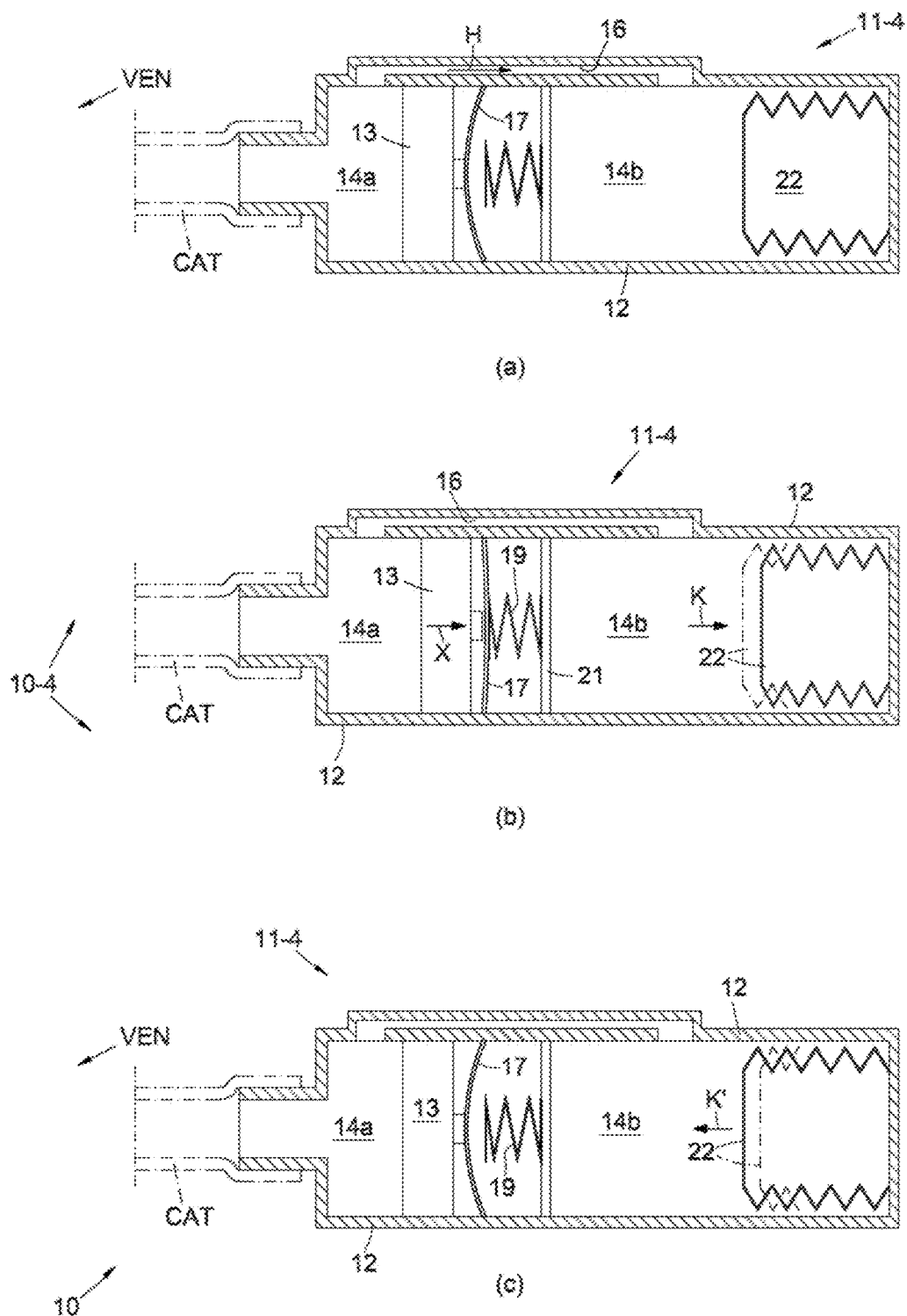
FIG. 7, divided into the sections (a)-(c), shows a fourth embodiment of the mechanical device of FIGS. 1 and 2, for the treatment of the hydrocephalus syndrome, in the various configurations taken on by the same device during its functioning.

This fourth and final embodiment, denoted by 10-4 and shown in FIG. 7, of the implantable device 10 of the invention, in which the parts corresponding to those of the embodiments already described will be denoted by the same reference numerals, does not provide, unlike the preceding 10-3, any drainage of the cerebrospinal fluid CSF.

Therefore the functioning of this device 10-4 is similar to that of the preceding 10-3, except for the fact that the reduction in the instantaneous systolic intracranial pressure ICP and the increase in the diastolic one, in order to achieve overall damping of the pulsation of the intracranial pressure ICP, are achieved by means of only the non-linear spring 17.

Naturally all the embodiments 10-1, 10-2, 10-3 and 10-4, described previously, of the implantable device 10 of the invention can be differently dimensioned and customised in order to take account of the various surgical needs and of the specific features of the patient in whom they are to be implanted.

In particular, the non-linear bistable spring 17 is appropriately calibrated and dimensioned, in the phase of manufacture of the mechanical valve devices 11-1, 11-2, 11-3, 11-4 of these embodiments 10-1, 10-2, 10-3, 10-4, so as to present the non-linear elastic characteristic required, therefore also the required and determined preset value of force which trips the spring 17 from one to the other of its two stable end positions passing through the instable intermediate position.

In this way the mechanical valve devices 11-1, 11-2, 11-3, 11-4 are appropriately dimensioned and calibrated in order to be made and built in various models, which can in turn be selected by the surgeon as a function of the surgical needs and of the specific features of the patient in whom these devices are to be implanted, in order to obtain in the patient affected by hydrocephalus the required reduction in the pulsatility of the intracranial pressure ICP.

It is therefore clear, from what is described, that the present invention achieves in full the objectives that had been set, and in particular proposes a device, implantable surgically, having an exclusively mechanical construction, therefore advantageously without electric or electronic devices and components, which is suitable for reducing and damping significantly the pulsations of the intraventricular or intracranial pressure which are induced by the systole and diastole cardiac cycle.

Figure 8:
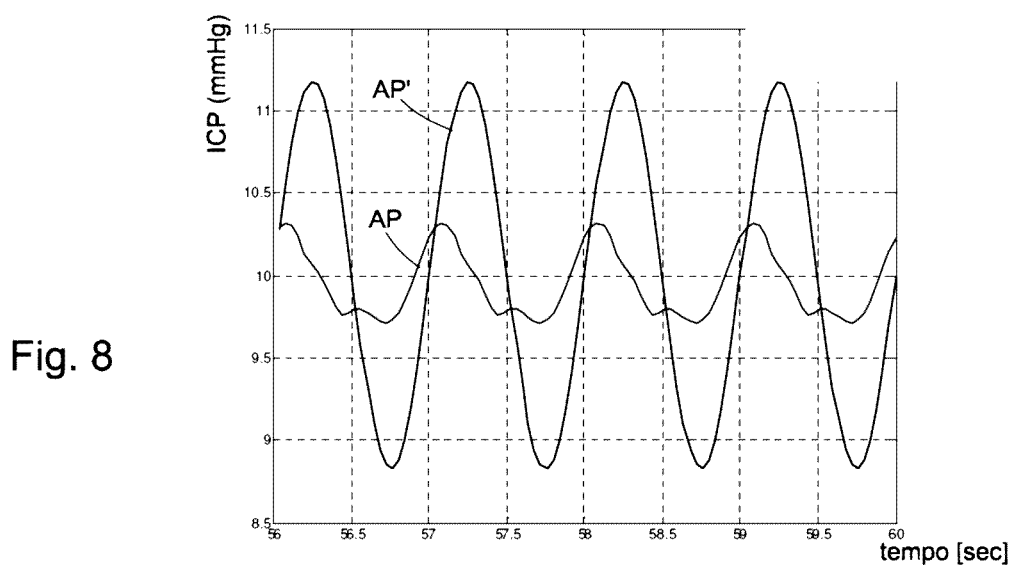
FIG. 8 is a diagram which shows qualitatively and compares the trend of the intracranial pressure which is obtained with the mechanical device of the invention with respect to the trend of the intracranial pressure which occurs in normal conditions without this device.

In particular FIG. 8 shows and compares the pulsating trend, denoted by AP, of the intracranial pressure ICP, determined by the systole and diastole cardiac phases, which is obtained with the device 10 of the invention implanted surgically in the patient affected by hydrocephalus, with the trend, denoted by AP', which occurs instead in normal conditions, i.e. in the absence of this device 10.

As can be observed the reduction in the variation of the intracranial pressure ICP, i.e. in the pulsatility of the intracranial pressure ICP due to the systole and diastole cardiac cycle, which is obtained with the device 10, is truly significant.

The invention claimed is:

1. Surgically implantable device for the treatment of hydrocephalus syndrome in a patient, characterised by a mechanical passive valve device designed to move and displace the cerebrospinal fluid or liquor in the cranial site of the patient in order to control the value of the actual intracranial pressure of said cerebrospinal fluid or liquor in said cranial site comprising:

an outer cylindrical body having a substantially cylindrical shape;

a piston slidably arranged in said cylindrical body so as to define within it two distinct chambers separated by said piston, a first chamber, frontal, of said two chambers being designed to communicate, via a catheter, with a ventricle of the cranial site, whereby the sliding piston receives, on a respective face adjacent to said first chamber, the pressure of the cerebrospinal fluid contained in the ventricle;

a capillary tube for enabling communication between said two chambers and thereby allowing the cerebrospinal fluid to flow between them, and a non-linear spring associated in said cylindrical body with said piston in order to control its position, wherein said non-linear spring has a special non-linear elastic characteristic designed to apply, on said piston, slidable, a corresponding elastic force such that, when the difference between the pressures applied by the cerebrospinal fluid on the two opposite faces of the piston is null, the piston is held in a rest position by said spring having said non-linear elastic characteristic;

when the difference of the pressures applied by the cerebrospinal fluid on the two opposite faces of the piston exceeds, during the phase of cardiac systole, a certain predetermined value set in the calibration phase of the mechanical valve device, the piston, due to the effect of said non-linear characteristic of the spring, moves rapidly in the cylindrical body towards the second chamber, rear, of said two chambers, resulting in a higher suction, by the same piston, of the cerebrospinal fluid contained in the ventricle, and, when the intracranial pressure falls below a certain value, during the phase of cardiac diastole, the piston, under the action and control of said non-linear spring, quickly returns back to the initial rest position, in order to infuse and re-enter in the cranial site the cerebrospinal fluid previously aspirated, so as to reduce, during the systolic phase, and to increase, during the diastolic phase, the value of the actual intracranial pressure in the ventricle, and thereby obtain, on the whole, a reduction or levelling of the intraventricular pulsatility, or of the change of the intracranial pressure in the ventricle, compared to the change that would occur in normal conditions in the absence of the device of the invention, while maintaining substantially unchanged and constant the average value of the intracranial pressure, wherein in said second chamber, rear, the cerebrospinal fluid is held at a reference pressure, substantially constant, by means of a conventional valve of the differential or threshold type, whereby the piston is subjected, on one face, to the pressure of the cerebrospinal fluid contained in the ventricle of the cranial site, and, on the opposite face, to said reference pressure, and the average value, constant, of the intracranial pressure is determined by said conventional valve of the differential or threshold type, and wherein said capillary tube is associated with a membrane valve designed to control the flow of the cerebrospinal fluid between the first chamber communicating with the ventricle of the cranial site and the second chamber containing the cerebrospinal fluid held at the constant reference pressure by said conventional valve of the differential or threshold type.

2. Implantable device for the treatment of hydrocephalus syndrome according to claim 1, wherein said mechanical valve device further comprises, in addition to said capillary tube, a bypass duct designed to put in communication said first and second chamber with each other, wherein said bypass duct is designed to be opened, so as to allow the flow of cerebrospinal fluid from the first to the second chamber, when the piston moves (X) during the systolic phase towards the second chamber, and wherein said bypass duct is designed to be closed, so as to prevent the flow of cerebrospinal fluid from the second to the first chamber, when the piston moves during the diastolic phase towards the first chamber.

3. Implantable device for the treatment of hydrocephalus syndrome according to claim 1, wherein said first chamber, frontal, of said mechanical valve device is associated, in addition to with the catheter which communicates with the ventricle of the cranial site, also with a further drainage catheter designed to drain the cerebrospinal fluid to the outside of the valve device.

4. Implantable device for the treatment of hydrocephalus syndrome according to claim 1, wherein said non-linear spring is in the form of a spherical cap.

5. Implantable device for the treatment of hydrocephalus syndrome according to claim 1, wherein said non-linear spring is constituted by a metallic lamina in the form of a cylindrical sector.

6. Implantable device for the treatment of hydrocephalus syndrome according to claim 1, wherein said non-linear spring is associated and coupled in said cylindrical body with a second spring exhibiting a linear elastic characteristic, wherein said second linear spring is designed to cooperate with said non-linear spring so as to apply on it a recovery action directed to facilitate and speed, during the diastolic phase, the displacement and the return of said non-linear spring from the end position reached following the systolic phase.

7. Implantable device for the treatment of hydrocephalus syndrome according to claim 6, wherein, when said non-linear spring is in the rest position at the beginning of the systolic phase, the device exhibits, between said non-linear spring and said second spring, a certain play that is recovered when said non-linear spring moves during the systolic phase.

8. Implantable device for the treatment of hydrocephalus syndrome according to claim 1, wherein said capillary tube is calibrated.

* * * * *